United States Patent [19]

Aeschbach et al.

[11] Patent Number: 5,026,550
[45] Date of Patent: Jun. 25, 1991

[54] PROCESS FOR THE PREPARATION OF AN ANTIOXYDANT EXTRACT OF SPICES

[75] Inventors: Robert Aeschbach, Vevey; Georges Philippossian, Lausanne, both of Switzerland

[73] Assignee: Nestec S.A., Vevey, Switzerland

[21] Appl. No.: 236,504

[22] Filed: Aug. 25, 1988

[30] Foreign Application Priority Data

Sep. 16, 1987 [CH] Switzerland .................. 3574/87

[51] Int. Cl.$^5$ .............................................. A61K 35/28
[52] U.S. Cl. .................................. 424/195.1; 426/542; 252/398
[58] Field of Search ........................ 424/195.1; 426/542; 252/398

[56] References Cited

U.S. PATENT DOCUMENTS

| 3,950,266 | 4/1976 | Chang et al. | 252/398 |
| 4,012,531 | 3/1977 | Viani | 426/431 |
| 4,352,746 | 10/1982 | Bracco et al. | 252/398 |
| 4,450,097 | 5/1984 | Nakatani et al. | 252/404 |

FOREIGN PATENT DOCUMENTS

| 038959 | 11/1981 | European Pat. Off. . |
| 2192852 | 2/1974 | France . |
| 2184341 | 6/1987 | United Kingdom . |

OTHER PUBLICATIONS

Translation of French Pat. No. 2,192,852, 1974, pp. 1–4.

*Primary Examiner*—John W. Rollins
*Attorney, Agent, or Firm*—Vogt & O'Donnell

[57] ABSTRACT

An antioxidant composition is obtained by subjecting a spice to at least one extraction with a non-polar solvent, after which the residue from the spice thus extracted is subjected to at least one extraction with a polar solvent and the extract obtained from each extraction with the polar solvent is concentrated and dried to obtain the antioxidant. Additionally, the extract obtained from the non-polar solvent extractions may be mixed with a basic aqueous solution, after which the aqueous phase of the mixture is acidified and then extracted with dichloromethane, and the extract so obtained may be combined with the extract obtained from the polar solvent extractions, concentrated and then dried.

17 Claims, No Drawings

PROCESS FOR THE PREPARATION OF AN ANTIOXYDANT EXTRACT OF SPICES

BACKGROUND OF THE INVENTION

This invention relates to a process for the production of a substantially odorless and neutral-tasting, antioxidant spice extract and to the use of this extract.

It is known that certain spices, such as rosemary and sage, have a high content of antioxidants. Processes have already been developed in the prior art to free the spices from all those components which do not contribute to the antioxidant activity.

EP 38959 discloses a process for the production of antioxidant and antibacterial preservatives, in which the base material, such as rosemary, is extracted with a mixture of polar and non-polar solvents, for example ethanol and n-hexane, to obtain the ready-to-use spice extract. The disadvantage of this process is that it does not give a spice extract totally freed from its bitterness and all its odoriferous components.

U.S. Pat. No. 4,450,097 discloses a process for the production of an antioxidant from rosemary, in which the spice is extracted with a non-polar solvent, the extract is subjected to steam distillation and the residue thus obtained is extracted with an aqueous alkaline solution having a pH value of at least 10.5. The disadvantage of this process is that it does not enable all the antioxidant material to be extracted from the rosemary.

SUMMARY OF THE INVENTION

The object of the process according to the invention is to prepare an odorless, neutral-tasting spice extract which may be considered for a wide variety of applications by utilizing the preservative character of the spice extract.

The present invention relates to a process for the production of a substantially odorless and neutral-tasting antioxidant spice extract, in which the spice is subjected to at least one extraction with a non-polar solvent, the spice thus treated is subjected to at least one extraction with a polar solvent and the extract phrase containing the polar solvent is concentrated and dried to obtain the spice extract.

In one embodiment which enables the degree of extraction of antioxidant materials to be increased, the extract obtained with the non-polar solvent may be treated. In this case, the extract is mixed with a basic aqueous solution, the aqueous phase is recovered, acidified and extracted with dichloromethane and the extract obtained is mixed with the phase obtained from the extraction with the polar solvent and the mixture obtained is evaporated and dried to obtain a spice extract having a high content of antioxidant material.

The treatment of the spice with a n on-polar solvent enables virtually all the odoriferous constituents of the spice to be extracted. The subsequent treatment of the non-polar extract with a base enables the antioxidant components to be recovered. The base used is preferably sodium hydroxide. The extraction of the spice with a polar solvent enables all the remaining components responsible for the antioxidant character to pass into the polar phase.

This embodiment of the process according to the invention gives a substantially odorless and colorless extract which contains all the antioxidant constituents available in the spice by virtue of the fact that an antioxidant product is reconstituted from two extracts which themselves show antioxidant properties.

DETAILED DESCRIPTION OF THE INVENTION AND PREFERRED EMBODIMENTS

In the context of the invention, non-polar solvents are understood to be optionally branched, optionally cyclized, saturated $C_5$-$C_8$ hydrocarbons and mixtures thereof, volatile aromatic hydrocarbons and chlorinated solvents, while polar solvents are understood to be $C_1$-$C_4$ alcohols, volatile ketones, acetone, methyl ethyl ketone and solvents of the ether and ester type. Hexane is preferably used as the nonpolar solvent and ethanol as the polar solvent.

The spice subjected to the treatment according to the invention may be both the whole spice and also spice residues, i.e., spices which have been subjected to steam distillation.

Depending on the starting product and the type of application envisaged, the spice is subjected to between 1 and 7 extractions with hexane and, similarly, to between 1 and 7 extractions with ethanol. These extractions normally take place between ambient temperature and the boiling point of the solvent, preferably at a temperature in the range from 20° to 30° C., with a ratio of spice to hexane and spice to ethanol for each extraction of from 1:1 to 1:10 (weight/volume). The extractions both with hexane and with ethanol are carried out over a period of from 30 minutes to 3 hours.

In order not to degrade the antioxidant materials, these extractions are carried out in the presence of an inert gas, for example nitrogen.

The process according to the invention gives a spice extract having a high content of antioxidant material. However, this extract is green in color. In some cases, it is of advantage, depending on the application envisaged, to prepare a colorless spice extract. In this case, the last extraction with ethanol is followed by decoloration with active carbon. This decoloration is carried out with an active carbon content of from 10 to 20% by weight, based on the end product. It has been found that the antioxidant power is less pronounced after decoloration than in a nondecolored spice extract.

Finally, the ethanol phase has to be concentrated and dried. The drying step is preferably carried out in vacuo over a period of about 10 hours at a temperature below 60° C. in order not to degrade the antioxidants present. In one variant, water is added to the concentrated ethanol solution and the drying step is carried out by spray-drying so that the spice extract is obtained in the form of a fine powder.

The spices tested in accordance with the invention are rosemary and sage.

Since the powder obtained by the process according to the invention has virtually no odor or taste, it may be considered of virtually any application both in the food industry and in the cosmetics and pharmaceutical field. It is incorporated in a quantity of 0.01 to 0.5% by weight, based on the weight of the product to be stabilized.

The process according to the invention is carried out either continuously or in batches, in countercurrent or by percolation.

Examples

The process according to the invention is illustrated by the following Examples.

EXAMPLE 1

Batch process 500 g rosemary residue (rosemary leaves which have been subjected to steam distillation) are extracted for 2.5 h at ambient temperature with 2.5 l hexane in a tank equipped with a mixer. After filtration, the extraction is repeated a second time under the same conditions. The two filtrates are combined and concentrated to a volume of 400 ml. This hexane extract is carefully stirred in a gentle stream of nitrogen with 400 ml of an aqueous sodium hydroxide solution (2-normal ). After 10 minutes, the aqueous phase is separated from the organic phase and immediately acidified with concentrated sulfuric acid and then extracted with dichloromethane to recover the antioxidant material. This treatment of the extract with hexane is repeated a second time under the same conditions and the two resulting dichloromethane extracts are combined.

The residue of rosemary treated with hexane as described above is extracted with 2.5 l ethanol while mixing under nitrogen for 2.5 h at ambient temperature. The alcoholic extract is filtered and decolored with 5g active carbon while mixing under nitrogen for 2.5 h at ambient temperature. After filtration on Celite, the extract is combined with the dichloromethane extract of the non-polar fraction and the resulting mixture is concentrated in a rotary evaporator and finally evaporated to dryness in a vacuum oven. 57 g of powder-form rosemary extract are obtained (yield: 11.4%).

EXAMPLE 2

The procedure is as in Example 1, except that the ethanol extract is not decolored with active carbon. The resulting rosemary extract corresponds to a yield of 12.4%.

EXAMPLE 3

Batch process 1 kg ground rosemary residue is mixed with 5 l hexane in a tank equipped with a mixer. After extraction under nitrogen for 2.5 h at ambient temperature, the hexane extract is filtered. The hexane phase is discarded and the operation is repeated under the same conditions as before. The residue thus recovered is mixed with 5 l ethanol mixed with 5% methanol. After extraction under nitrogen with stirring for 2.5 h at ambient temperature, the product is filtered to recover 4.7 l alcohol containing the antioxidant materials. The alcoholic extract is then decolored with 20 g active carbon for 2.5 h under nitrogen at ambient temperature. After filtration, 4.6 liters ethanol remain and are concentrated in a rotary evaporator to 0.4 l and, finally, evaporated in vacuo (12 mm Hg) to dryness for 15 h at 50° C. 96.5 of powder-form rosemary extract are obtained (yield 9.65%).

EXAMPLE 4

Countercurrent process 1 l hexane is mixed with 1 kg ground rosemary residue. 4 l hexane which have already been used to extract two other batches of rosemary and contain 21 g waxes are then passed over the resulting mixture. After this extraction, the 4 liters of hexane contain 47 g waxes. A second extraction is carried out with 4 liters hexane which have already been used to extract another batch of rosemary and contain 8 g waxes. Thereafter, this volume of hexane contains 21 g waxes. A third extraction is carried out with 4 liters of fresh hexane which, thereafter, contain 8 g waxes.

The rosemary residue is left to dry and is then mixed with 1 l ethanol. 3 l ethanol which have already been used to extract another batch of rosemary are then passed over this mixture, containing 45 g rosemary extract before passage and 105 g rosemary extract thereafter. A second extraction is carried out with 3 l fresh ethanol which then contains 45 g crude extract. The rosemary thus extracted is discarded. The 3 l ethanol containing 105 g extract are then decolored with active carbon, filtered, concentrated and evaporated to obtain 95 g of powder-form rosemary extract ready for use (yield 9.5%).

EXAMPLE 5

Percolation process 500 g of rosemary residue are placed in a chromatography column. 1250 ml hexane are added and the rosemary residue is extracted by percolation, the hexane being recirculated through the column for 30 minutes (throughput: 750 ml/h). The hexane containing the waxes is then drained for 15 minutes and the resulting 750 ml extract are replaced by fresh hexane. The operation is repeated 6 times in the same column.

The residue is left to dry in a gentle stream of nitrogen and is extracted in the same column by percolation with 1250 ml ethanol recirculated for 30 minutes at ambient temperature. The ethanol is then drained for 15 minutes and the resulting 750 ml extract are replaced by fresh ethanol. This extraction with ethanol is repeated six times. The seven ethanol extracts are combined, concentrated to half the volume, decolored for 2.5 h on active carbon and, after filtration, dried in vacuo. The rosemary extract obtained (52.5 g dry powder) corresponds to a yield of 10.5%.

EXAMPLE 6

The procedure is as in Example 3 without decoloration of the ethanol extract. Yield: 10.5%.

EXAMPLE 7

The procedure is as in Example 3, except that sage (distilled with steam) is used as the starting material. Yield 12.4%.

The following Table shows the yields, antioxidant activities and organoleptic properties of the extracts obtained in accordance with Examples 1 to 7. These data are compared with those of three extracts of rosemary or sage residue which have been obtained simply by extraction with ethanol (ratio of spice to ethanol 1:5 (weight/volume)) for 2.5 h at ambient temperature with or without decoloration.

TABLE

| Extract | Extraction yield % by weight | Antioxidant index (a) | Antioxidant value (b) | Odor (c) | Bitterness (c) | Color |
|---|---|---|---|---|---|---|
| Ex. 1 | 11.4 | 4.3 | 49.2 | — | — | beige |
| Ex. 2 | 12.7 | 4.9 | 62.2 | — | — | greenish |

TABLE-continued

| Extract | Extraction yield % by weight | Antioxidant index (a) | Antioxidant value (b) | Odor (c) | Bitterness (c) | Color |
|---|---|---|---|---|---|---|
| Ex. 3 | 9.65 | 3.7 | 35.7 | (+) | — | yellowish |
| Ex. 4 | 9.5 | 3.6 | 34.2 | — | — | beige |
| Ex. 5 | 10.5 | 3.5 | 36.75 | — | — | beige |
| Ex. 6 | 10.5 | 4.2 | 44.1 | — | — | greenish |
| Ex. 7 | 12.4 | 4.8 | 59.5 | + | + | green |
| Ethanolic extract of rosemary residue | 11.9 | 3.9 | 46.4 | +++ | ++ | dark green |
| Decolored ethanolic extract of rosemary residue | 10.1 | 3.6 | 36.35 | ++ | ++ | green |
| Ethanolic extract of sage residue | 14.2 | 4.4 | 62.5 | +++ | ++ | dark green |

(a) Antioxidant index: Rancimat test (500 ppm extract, chicken fat, 110° C., air: 20l/h)
(b) Antioxidant value: Product of EY × AI  EY = extraction yield  AI = antioxidant index
(c) Evaluation criteria − virtually no odor/no bitterness + some odor/slightly bitter + + odoriferous/bitter +++ highly odoriferous/very bitter

We claim:

1. A process for preparation of an antioxidant composition comprising extracting a spice selected from a group of spices consisting of rosemary and sage at least once with a nonpolar solvent thereby obtaining a first extract and an extracted residue, separating the first extract from the extracted residue, extracting the extracted residue at least once with a polar solvent thereby obtaining a second extract, concentrating the second extract and then drying the concentrated extract for obtaining an antioxidant composition.

2. A process according to claim 1 further comprising mixing the first extract with a basic aqueous solution thereby forming an aqueous phase and a non-polar solvent phase, separating the aqueous phase and the non-polar solvent phase, acidifying the aqueous phase, extracting the acidified aqueous phase with dichloromethane for obtaining a third extract, mixing the third extract with the second extract and then concentrating the second extract and third extract mixture and drying the concentrated mixture for obtaining the antioxidant composition.

3. A process according to claim 1 or 2 wherein the polar solvent and non-polar solvent extractions are carried out in the presence of an inert gas.

4. A process according to claim 1 or 2 wherein the non-polar solvent is selected from a group of non-polar solvents consisting of saturated $C_5$–$C_8$ hydrocarbons and mixtures thereof, volatile aromatic hydrocarbons and chlorinated solvents.

5. A process according to claim 1 or 2 wherein the polar solvent is selected from a group of polar solvents consisting of $C_1$–$C_4$ alcohols, volatile ketones, acetone, methyl ethyl ketone, ether solvents and ester solvents.

6. A process according to claim 1 or 2 wherein the non-polar solvent is hexane and the polar solvent is ethanol.

7. A process according to claim 6 wherein the extractions are carried out at a temperature of from 20° C. to 30° C.

8. A process according to claim 6 wherein the extractions are carried out from 30 minutes to 3 hours.

9. A process according to claim 6 wherein each spice extraction has a ratio of spice to hexane and spice to ethanol of from 1:1 to 1:10 (weight/volume).

10. A process according to claim 6 wherein between 1 and 7 extractions are carried out with the non-polar solvent hexane.

11. A process according to claim 6 wherein between 1 and 7 extractions are carried out with the polar solvent ethanol.

12. A process according to claim 1 or 2 further comprising decoloring the second extract with active carbon.

13. A process according to claim 1 or 2 wherein the drying step is carried out in vacuo.

14. A process according to claim 1 or 2 wherein the drying step is carried out by spray drying.

15. A process according to claim 1 or 2 wherein the rosemary spice is a rosemary residue obtained from steamed distilled rosemary leaves.

16. A process for the production of an antioxidant composition comprising extracting a spice selected from a group of spices consisting of rosemary and sage at least once with hexane thereby obtaining a first extract and an extracted residue, separating the first extract from the residue, extracting the residue at least once with ethanol thereby obtaining a second extract, mixing the first extract with a basic aqueous solution thereby forming an aqueous phase and a non-polar solvent phase, separating the aqueous phase and the non-polar solvent phase, acidifying the aqueous phase, extracting the acidified aqueous phase with dichloromethane for obtaining a third extract, mixing the third extract with the second extract and then concentrating the second extract and third extract mixture and drying the concentrated mixture for obtaining an antioxidant composition.

17. A process according to claim 16 wherein the extractions are carried out at a temperature of from 20° C. to 30° C. for from 30 minutes to 3 ours and wherein each spice extraction has a ratio of spice to hexane and spice to ethanol of from 1:1 to 1:10 (weight/volume) and further comprising carrying out the spice extractions in the presence of an inert atmosphere.

* * * * *